United States Patent
Merchant et al.

(10) Patent No.: US 7,014,657 B1
(45) Date of Patent: *Mar. 21, 2006

(54) MIDDLE-EAR IMPLANT

(75) Inventors: Saumil N. Merchant, Acton, MA (US); Joseph B. Nadol, Jr., Needham, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 890 days.

This patent is subject to a terminal disclaimer.

(21) Appl. No.: 09/625,644

(22) Filed: Jul. 26, 2000

Related U.S. Application Data

(63) Continuation-in-part of application No. 09/362,272, filed on Jul. 28, 1999, now Pat. No. 6,251,138.

(60) Provisional application No. 60/146,067, filed on Jul. 28, 1999.

(51) Int. Cl.
  *A61F 2/18* (2006.01)
  *A61F 2/04* (2006.01)

(52) U.S. Cl. .................... 623/10; 623/11.11; 623/23.64

(58) Field of Classification Search ................ 623/10, 623/11.11, 23.64; 604/96–103, 49, 892.1; 600/37; 128/898
See application file for complete search history.

(56) References Cited

U.S. PATENT DOCUMENTS

| | | | |
|---|---|---|---|
| 4,297,748 A | 11/1981 | Moloy | 3/1 |
| 4,470,407 A | 9/1984 | Hussein | 128/6 |
| 5,356,430 A | 10/1994 | Nadol, Jr. | 623/10 |
| 5,480,433 A | 1/1996 | Nadol, Jr. | 623/10 |

*Primary Examiner*—David J. Isabella
(74) *Attorney, Agent, or Firm*—Fish & Richardson P.C.

(57) ABSTRACT

This invention relates to surgical methods and prosthetic devices for ameliorating hearing loss in patients having ailments of the middle ear. The implant of the invention includes a gas-filled balloon having a pliant membrane of biocompatible material. The balloon is made such that the acoustic impedance presented by the balloon to the eardrum is low enough to permit the eardrum to vibrate freely in response to sound waves. Because the balloon membrane is substantially impermeable to gases and water, the implant can function effectively within the middle-ear chamber for an extended period.

25 Claims, 4 Drawing Sheets

US 7,014,657 B1

MIDDLE-EAR IMPLANT

RELATED APPLICATIONS

This application is a continuation-in-part of U.S. patent application Ser. No. 09/362,272 filed on Jul. 28, 1999, now U.S. Pat. No. 6,251,138, the contents of which are herein incorporated by reference. This application claims the priority date of U.S. Provisional Patent Application No. 60/146,067, filed on Jul. 28, 1999 the contents of which are herein incorporated by reference.

BACKGROUND

The middle-ear includes a chamber that is bounded on one side by the eardrum and on another other side by the cochlea of the inner ear. In a healthy middle ear, this chamber is filled with air. A narrow passageway, called the eustachian tube, ensures that the static air pressure within the middle-ear chamber is equal to the ambient pressure.

Three very small bones, referred to as "ossicles," provide a mechanical connection between the eardrum and the inner ear. The first and third ossicles are mechanically coupled to the eardrum and to the inner ear respectively. The second ossicle provides a mechanical linkage between the first and third ossicles.

The sensation of hearing results from sound waves that set the eardrum into motion. The motion of the eardrum, in turn, causes the three ossicles to vibrate. These three ossicles thus carry the vibrations across the air-filled chamber to the inner ear, where they are converted into an electrical signal that is recognizable by the brain. Because the transmission of sound across the air-filled chamber depends heavily on the vibration of the eardrum and the ossicles, it is essential that these structures remain free to vibrate at all times.

Certain diseases interfere with the free vibration of these structures. For example, otitis media, which is an inflammation of the middle-ear, can result in accumulation of fluid in the middle-ear chamber. If the eustachian tube cannot clear this fluid, the chamber will fill with fluid. Otitis media can also result in the build up of fibrous tissue within the chamber. Because this fibrous tissue is not a fluid, it cannot drain through the eustachian tube at all.

To appreciate the impact of fluid or fibrous tissue in the middle-ear chamber, it is useful to consider the operation of an air-filled kettledrum. When struck by a drumstick, the drum skin freely vibrates. This results in a deep and resonant sound. On the other hand, if instead of being filled with air, the kettledrum were to be filled with viscous fluid or cotton batting, and then struck with a drumstick, the resulting sound would be muffled. This muffling occurs, in part, because the material that now fills the kettledrum impedes the free vibration of the drum skin.

The presence of fluid in the middle-ear chamber also interferes with wave propagation in the inner ear. In normal operation, the vibration of the ossicles causes a pressure wave in the fluid filled cochlea of the inner ear. This wave propagates to the far end of the cochlea, activating hair cells and nerve endings as it does so. The propagation of this wave is made possible by pressure release at the other end of the cochlea. This pressure release is achieved by a flexible membrane, referred to as the "round window membrane," that separates the fluid-filled interior of the cochlea from the normally air-filled middle-ear chamber. Any fluid collecting in the middle-ear chamber interferes with the pressure-release function of the round window membrane.

Nadol Jr. U.S. Pat. No. 5,356,430, the contents of which are herein incorporated by reference, teaches the placement of a gas-filled balloon within the middle-ear chamber in order to displace fluid and to allow motion of the round window membrane. However, the trilayer membrane of the balloon and the placement of the balloon within the middle-ear chamber near the round window membrane as taught in Nadol Jr. results in only limited improvement of middle-ear function.

SUMMARY

The present invention is based on a recognition of the importance of low acoustic impedance in a middle-ear balloon implant. The invention provides a gas-filled balloon adapted for placement in the middle-ear chamber with at least a portion of the balloon being in contact with the eardrum. The balloon is formed from a pliant membrane that has an acoustic impedance low enough to permit the eardrum to freely respond to incident acoustic waves. Preferably, the acoustic impedance is such that the balloon responds as would an air bubble having a volume no less than 70% of the balloon's volume.

The pliant membrane of the balloon can be made of a biocompatible polymeric film, preferably free of plasticizers or additives that may impart cytotoxicity. Suitable materials include homopolymers or copolymers of isobutylene, polystyrene, vinyledene chloride, ethylene terephthalate, ethylene-vinyl alcohol or acrylo-nitrile. The pliant membrane can be a single film or a multilayer film in which only the layer exposed to the middle-ear environment need be biocompatible.

Since the balloon is surgically inserted into the middle-ear, it is preferable that it remain functional for extended periods. Hence, it is preferable that the pliant membrane be relatively impermeable to gases and liquids present in the middle-ear chamber.

The manner in which the balloon is surgically inserted into the middle-ear chamber involves manipulation of the balloon by a surgeon. Because of the balloon's fragility, it is preferable that the balloon be provided with an optional tab. By grasping this tab, a surgeon can adjust the balloon's position in the middle-ear chamber. Such a tab is preferably radio-opaque.

Depending on the patient's anatomy and condition, it may be advantageous to insert more than one balloon in the middle-ear chamber. Consequently, the invention also includes an implant in which a plurality of balloons are placed in the middle-ear chamber, with at least one of the balloons contacting the eardrum. The balloons collectively present a low acoustic impedance to the eardrum, thereby enabling the eardrum to vibrate freely in response to incident sound waves.

In accord with another aspect of the invention, the balloon contains at least one large-molecule biocompatible gas, such as sulfur hexafluoride ($SF_6$). The balloon can also contain at least one naturally occurring atmospheric gas having a partial pressure below its normal partial pressure in the atmosphere. The total pressure of the gas within the synthetic balloon is preferably in a range of approximately 50 mm of $H_2O$ below the atmospheric pressure to approximately 50 mm of $H_2O$ above the atmospheric pressure.

The invention also includes a surgical method for treating middle-ear hearing loss of a patient. In the surgical method of the invention, a balloon is positioned against the eardrum in the patient's middle ear. The balloon is formed of a thin pliant membrane of biocompatible material and has an impedance low enough to permit sound-induced motions of the eardrum, ossicles and the round window membrane. The pliant membrane is substantially impermeable to water and to gases during extended contact with body fluids.

These and other features of the invention will be apparent from the following detailed description and the accompanying figures, in which:

BRIEF DESCRIPTION OF THE FIGURES

FIG. 4C is a cross-section view, along the line AA', of the implant of FIG. 4A;

DETAILED DESCRIPTION

Figure 1:
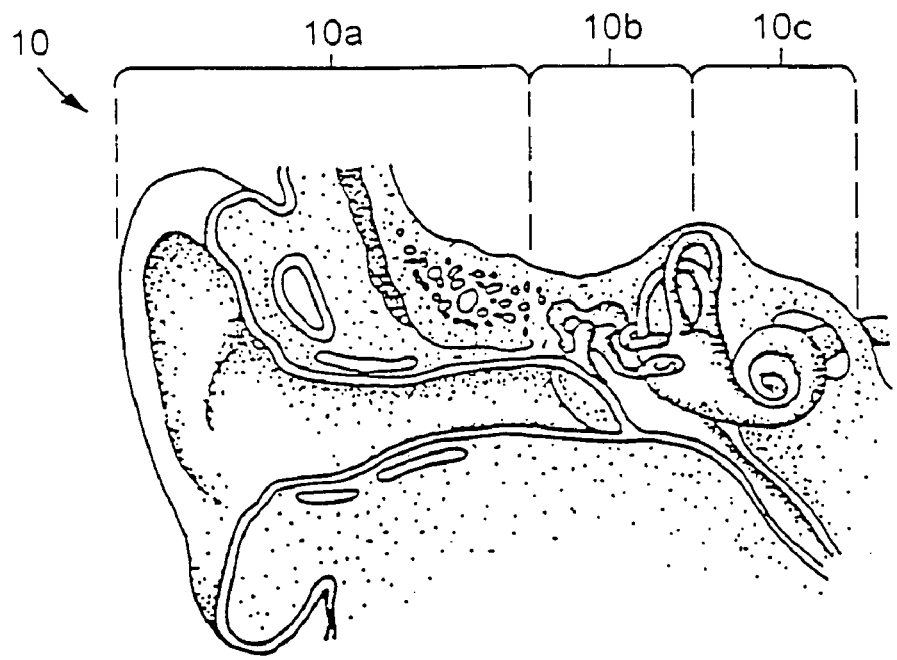
FIG. 1 schematically illustrates the anatomy of the human ear.
Figure 2:
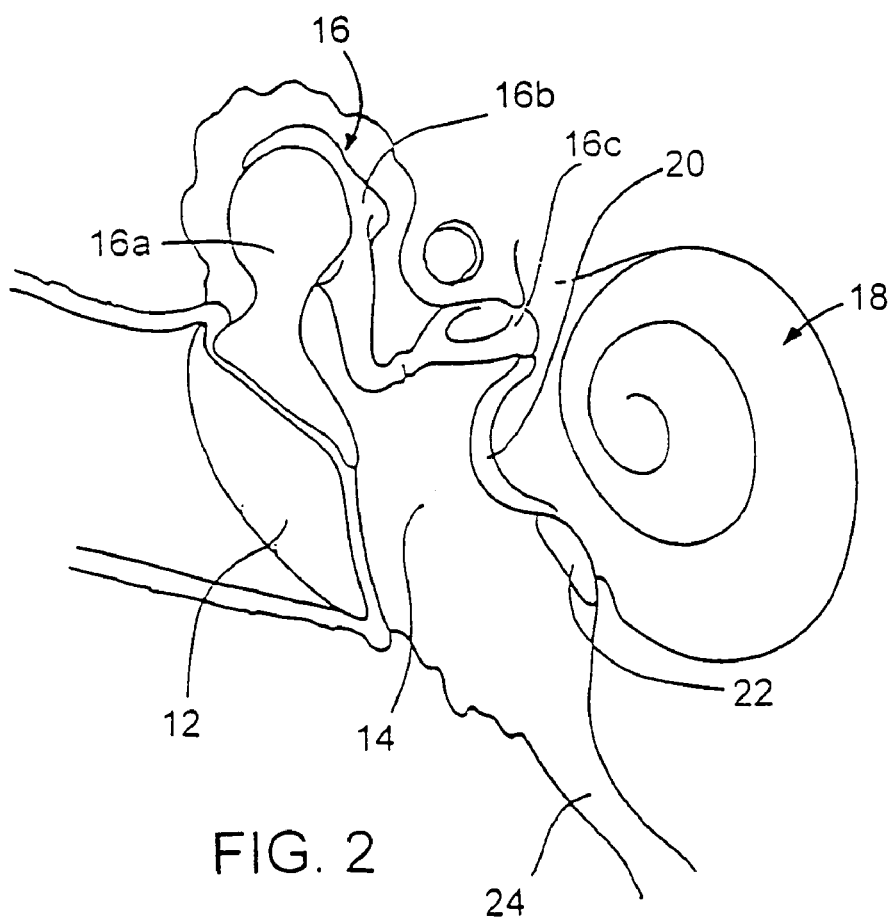
FIG. 2 is an enlarged detail view of the anatomy of the middle ear.

The present invention provides surgical methods and implants for relieving conductive hearing loss caused by diseases of the middle ear. FIGS. 1 and 2 illustrate the anatomy of the human ear 10, in which the auricle, ear canal and drum of the outer ear 10a transmit sound through the middle ear 10b to sensing structures of the inner ear 10c.

FIG. 2 illustrates an enlarged detail view of the structures of the middle ear 10b, as shown in FIG. 1, and their relative sizes and positions. The illustrated structures include the eardrum 12 (tympanic membrane), the middle-ear chamber 14, the ossicles 16, the cochlea 18, and the promontory 20. The illustrated structures further include a round window membrane 22 and a eustachian tube 24 for connecting the middle-ear chamber 14 to the ambient air by way of the nasopharynx. The ossicles 16 include the hammer, or malleus bone 16a, the anvil, or incus bone 16b, and the stirrup, or stapes bone 16c.

The middle-ear chamber 14, is ordinarily filled with air. Because the middle-ear chamber 14 is in communication with the atmosphere through the eustachian tube 24, the pressure in the middle-ear chamber 14 is normally equal to the ambient pressure.

Certain diseases can result in the middle-ear chamber 14 becoming chronically filled with fluid or fibrous tissue, thereby causing a conductive hearing loss. For example, if the eustachian tube 24 is obstructed or is otherwise dysfunctional, a pressure imbalance may occur that causes fluid to exude from the surrounding tissue. Alternatively, the middle-ear chamber 14 may fill with fibrous tissue caused by post-operative tissue deposition. Infections or inflammatory processes can likewise result in fluid or fibrous tissue build-up in the middle-ear chamber 14.

In certain middle-ear diseases, the normally air-filled middle-ear chamber 14 can become pathologically altered, resulting in undesirable conditions such as: retraction of the eardrum 12, inflammatory response in the middle ear, or retention of fluid in the middle-ear chamber 14. These conditions can all lead to a conductive hearing loss due to the pathologically induced inefficiency of the sound transmitting system of the middle ear. This is a common finding in chronic active and chronic inactive otitis media (COM), and in otitis media with effusion (OME). In particular, when the eardrum 12 is in contact with a transmission medium other than air, the transmission medium damps the vibration of the eardrum 12.

In effect, the eardrum 12 of a healthy middle ear 10b (FIG. 1) is coupled to a transmission medium having a low acoustic impedance. In contrast, in a diseased middle ear 10b, the eardrum 12 is coupled to a transmission medium having a high acoustic impedance. The middle-ear implant of the invention is intended to recouple the eardrum 12 to a low impedance medium by placing the eardrum 12 in contact with a gas-filled balloon in which the properties of the balloon's wall are selected to provide the eardrum 12 with a low impedance coupling.

Figure 3:
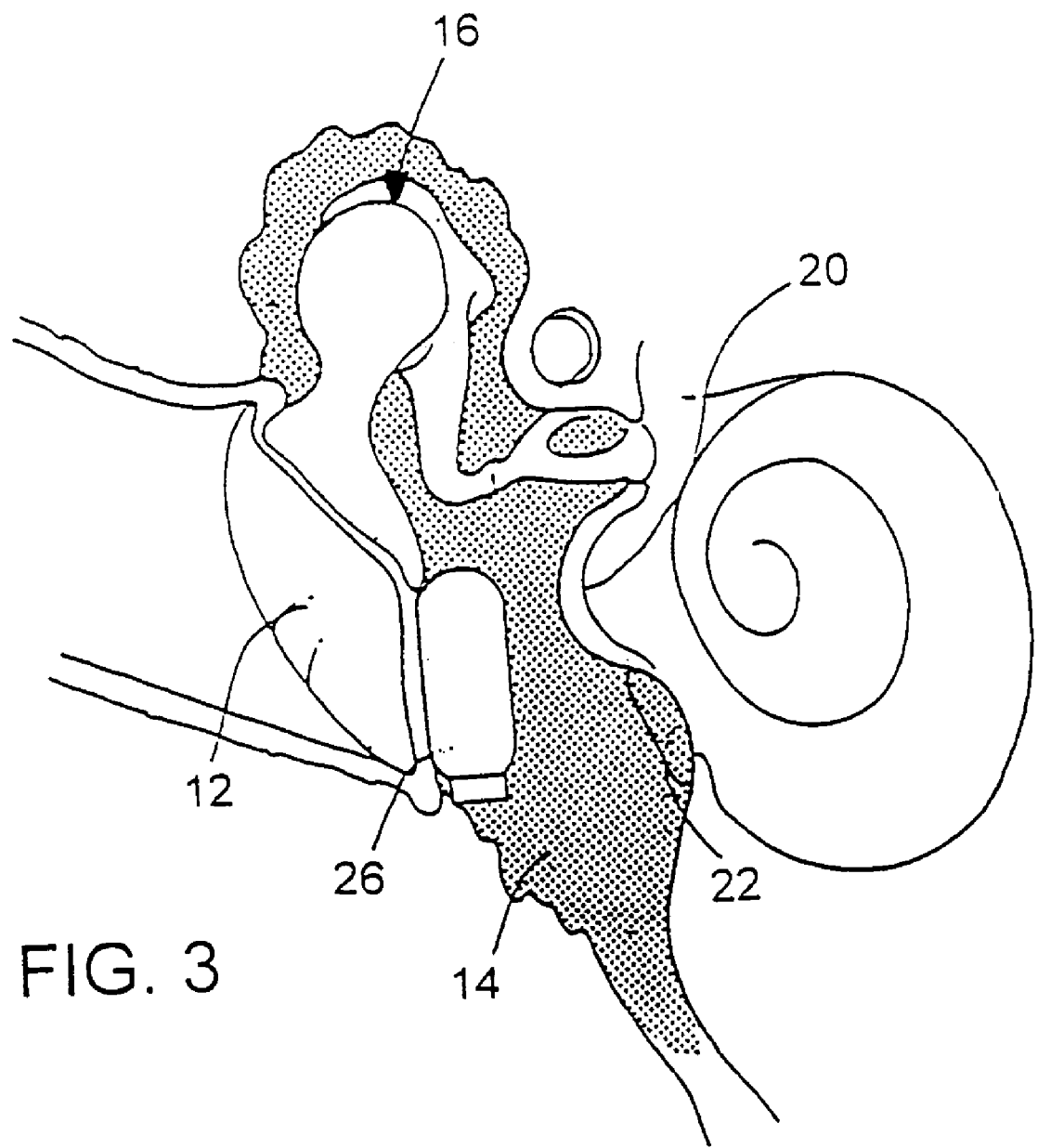
FIG. 3 illustrates an embodiment of an implant in its operative position adjacent to the eardrum.

FIG. 3 shows one aspect of the present invention in which an implant in the form of a balloon 26 encloses a compressible gas. The balloon 26 is surgically placed in the middle-ear chamber 14 so that it contacts the eardrum 12. Because the balloon membrane is pliant, and because the enclosed gas is relatively transparent to sound waves, the balloon 26 presents a relatively low acoustic impedance to the eardrum 12. As a result, the eardrum 12 is almost as free to vibrate in response to incident sound waves as it would have been had the middle-ear chamber 14 been filled with air. In effect, the balloon 26 replaces the high-impedance load associated with the non-gaseous transmission media present in the diseased middle-ear 10b with the lower impedance load of the balloon 26.

Figure 4A:
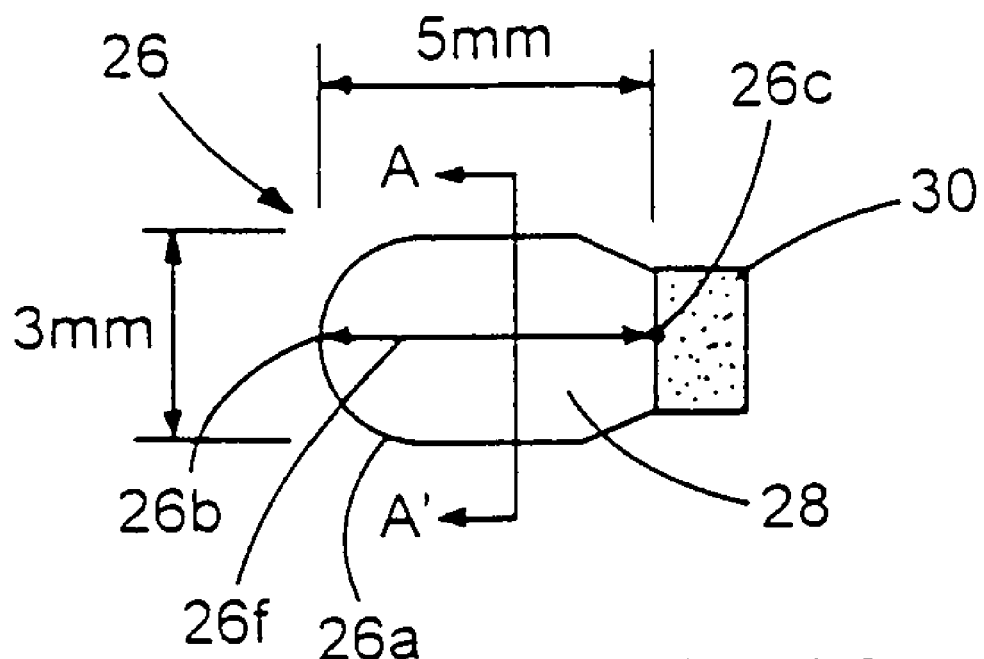
FIGS. 4A–4B are top view and side cross-sectional views of the implant of FIG. 3.
Figure 4B:
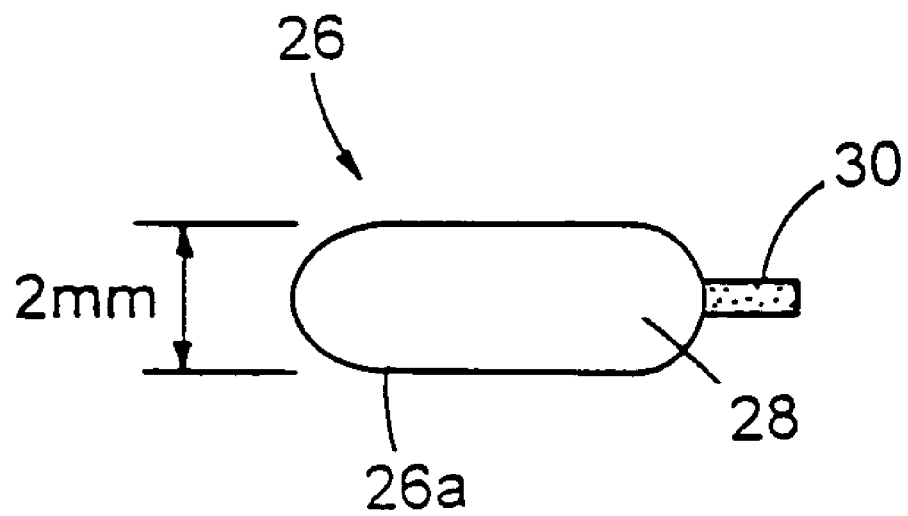

The preferred shape of the balloon 26, as shown in FIGS. 4A, 4B, and 4C, is that of a generally convex jelly bean or gelatin capsule. The illustrated balloon 26 includes a pliant membrane 26a enclosing an ovaloid gas-filled volume 28. The balloon 26 has a generally elliptical cross-section along the line AA' (FIG. 4C) with a major axis 26d having a length of approximately 3 mm and a minor axis 26e having a length of approximately 2 mm. Further, the balloon 26 has a principal axis 26f having a length of approximately 5 mm (FIG. 4A) extending from a first end 26b of the balloon 26 to a second end 26c thereof. These dimensions are selected to assure that the balloon 26 will fit in the middle-ear chamber 14.

A tab 30 extends from the second end 26c of the gas-filled volume 28 to provide a handle for surgical manipulation of the balloon 26. The tab 30 enables a surgeon to manipulate the balloon 26 without having to touch the balloon membrane 26a. This reduces the likelihood of damage to the balloon 26. The tab 30 preferably contains a filler material, such as barium, iodide, or metallic foil, which renders it radio-opaque for radiographic visualization. Alternatively, the balloon 26 can be rendered opaque by placing a metallic ribbon inside the balloon.

In general, the acoustic impedance of the balloon 26 is not as low as the acoustic impedance of an equal volume of air. This is because the membrane 26a from which the balloon 26 is made still has a modest dampening effect on the vibrations of the eardrum 12. Nevertheless, by suitable choice of a material for the membrane 26a, the dampening effect of the membrane 26a can be reduced sufficiently to provide significant improvement in hearing.

The acoustic impedance of the balloon 26 is measured in terms of its "equivalent volume." For a fixed temperature and pressure, the equivalent volume is defined as that volume of air whose acoustic impedance equals that of the balloon 26. The equivalent volume of the balloon 26 depends on the volume of the gas within the balloon 26, the choice of gas, the stiffness of the material comprising the balloon membrane 26a, the thickness of the membrane 26a, and the construction of the membrane 26a. Throughout this specification, the equivalent volume is expressed in terms of a percentage of the balloon's actual volume.

The balloon 26 is functionally equivalent to an air bubble having a size equal to the balloon's equivalent volume. As the equivalent volume of a balloon increases, its acoustic impedance decreases, and hence its compressibility increases. Accordingly, an increase in the equivalent volume of the balloon 26 increases its effectiveness as an implant for ameliorating conductive hearing loss.

The equivalent volume of the balloon 26 is preferably greater than or equal to approximately 70% of its actual volume. For example, in one preferred practice of the invention the balloon 26 has a volume of approximately thirty microliters. In such a case, the stiffness and thickness of the pliant membrane 26a are selected such that the balloon 26 has an equivalent volume that is greater than or equal to approximately twenty-one microliters. An equivalent volume of twenty-one microliters corresponds to an acoustic compliance of $1.5 \times 10^{-13} m^3/pascal$.

In addition to the requirement of low acoustic impedance, the preferred balloon 26 has several other properties. Because the implanted balloon 26 is to be in intimate contact with the biological environment of the middle-ear for extended periods, it is preferable that the material from which the balloon 26 is made be biocompatible. Because the balloon 26 is to remain inflated during that extended period, it is preferable that the material from which the membrane 26a is made also be an effective barrier to the diffusion of gas and water.

The balloon membrane 26a preferably has sufficient strength to avoid rupture or leakage when exposed to normal variations in static pressure encountered in commercial air travel. For example, during commercial airplane travel, the cabin pressure drops by roughly 15.5 cm Hg (to 60.8 cm Hg absolute). This corresponds to the atmospheric pressure at an altitude of 6000 feet. This reduction in pressure allows the balloon 26 to expand by as much as 25% in volume, or 8% in diameter.

To some extent, there exists a trade-off between the strength and impermeability of the balloon membrane 26a and its acoustic compressibility. A balloon membrane 26a with high burst strength and low permeability is likely to be somewhat thick and stiff, whereas one with high compressibility is likely to be somewhat leaky.

A membrane 26a suitable for use as a balloon implant can be made of a polyvinylidene chloride (PVDC) film. Such films are commercially available and widely used by the food-packaging industry. PVDC film can be made of a PVDC homopolymer, in which all the monomers are vinylidene chloride (VDC), or a PVDC copolymer, in which some of the VDC monomers are replaced. The replacement monomers in a PVDC copolymer can include methyl-acrylate and acrylo-nitrite.

PVDC films are substantially impermeable to air and oxygen and have excellent water barrier properties. A PVDC film having a thickness of approximately 1 mil results in a balloon 26 having an equivalent volume of greater than 70%, which is within a range that results in significant improvement in hearing.

In their pure form, PVDC films show minimal cytotoxicity. However, many commercially available PVDC films include additives and plasticizers that are added to the PVDC during the production process. These additives and plasticizers appear to impart some cytotoxicity. Hence, it is preferable that a PVDC film for use in the implant be free of such additives and plasticizers. As an alternative, the balloon 26 can include an external layer of a biocompatible material (e.g. polytetrafluoroethylene, gold, polyurethane) to insulate the middle-ear environment from contact with the additives and plasticizers.

Materials other than PVDC that possess the desirable barrier and acoustic compressibility properties can also be used for the membrane 26a of the balloon 26. Examples include polymeric films made of polyethylene terephthalate (PET), ethylene vinyl alcohol (EVOH), acrylonitrile (AN), poly-isobutylene (PIB), and polystyrene (PS). Like PVDC, PET, EVOH and AN are used in the food-packaging industry and can be formed into thin films. Polyisobutylene (PIB) polymers which are used in making vascular grafts, are biocompatible and also substantially impermeable to fluids and gases.

One practice of the invention employs film casting to prepare a film of pure polymer that is free of additives and plasticizers. In this practice of the invention, the polymer is dissolved in a non-toxic solvent and the resulting solution is spun cast onto a glass substrate in a clean room. The concentration of the solution is selected to produce spun cast films having a thickness between about 1 mil and about 4 mils. The spun-cast films are vacuum dried to remove residual solvent. The dried film is then peeled off the glass substrate to obtain a free-standing film. The film is then draped over a polished steel or glass mandrel to create a balloon pre-form. The mandrel is removed, after which the balloon is filled with gas and sealed at its open end to form the tab 30.

An alternative method for fabricating the balloon 26 includes solvent casting. In the solvent casting method, a mandrel is dipped into a solution of the polymer material from which the balloon membrane 26a is to be made. This results in the casting of a shell having a thickness between approximately 1 mil and approximately 4 mils. Following the casting, the shell is peeled from the mandrel, filled with gas, and sealed at its open end to form the tab 30.

In yet another method for fabricating the balloon, referred to as blow casting, a solution of the material to be formed into the membrane is passed through an annular void of an annular tube. At the same time, air is blown through the circular void in the center of the annular tube. As the solution exits the annular void, the air blowing through the circular void causes the annular stream of solution to balloon outward and to solidify.

The total pressure of the gas within the balloon is preferably the same as the atmospheric pressure, but can be in the range of approximately 50 mm of water below the atmospheric pressure to approximately 50 mm of water above the atmospheric pressure. In one preferred construction, the balloon is initially filled with a substantial portion (for example, 10–50% or more) of gas that is not normally present in the atmosphere. Preferably, this non-naturally occurring gas is one to which the balloon wall is substantially impermeable. An example of a suitable non-naturally occurring gas is sulfur hexafluoride ($SF_6$). In this embodiment, gases that naturally occur in the atmosphere, such as nitrogen and oxygen, are also present in the balloon but at lower partial pressures than in the surrounding atmosphere. After implantation of the balloon in the middle ear, the non-naturally occurring gas slowly diffuses out of the balloon. As it does so, naturally occurring gases dissolved in the middle-ear fluid diffuse into the balloon at a rate slightly exceeding the rate at which the non-naturally occurring gas diffuses out of the balloon. Thus, the balloon, over the course of a few months, spontaneously self-inflates, and remains inflated for as long as more than one to two years.

Referring again to FIG. 3, the implantation of the balloon 26 in the middle ear in contact with the eardrum 12 provides a number of advantages. In particular, the balloon 26 provides an air cushion on the side of the eardrum 12 facing the middle-ear chamber 14. Such an air cushion enables the eardrum 12 to vibrate freely in response to incident sound waves. Accordingly, the implanted balloon 26 advantageously enhances hearing of patients suffering from middle ear diseases, such as those resulting from dysfunction of the eustachian tube 24. In particular, the implanted balloon 26 enhances hearing of patients suffering from chronic otitis media (COM) and/or otitis media with effusion (OME).

As a result of its low permeability to gases and to fluids, the implanted balloon 26 remains inflated for long periods, and hence advantageously provides long term relief. In addition, the balloon 26 keeps the eardrum 12 intact, thus obviating the need for water precautions and reducing the risk of repeated infections, both of which are problems associated with the conventional use of ventilation tubes placed in the eardrum to provide aeration of the middle ear.

Figure 5:
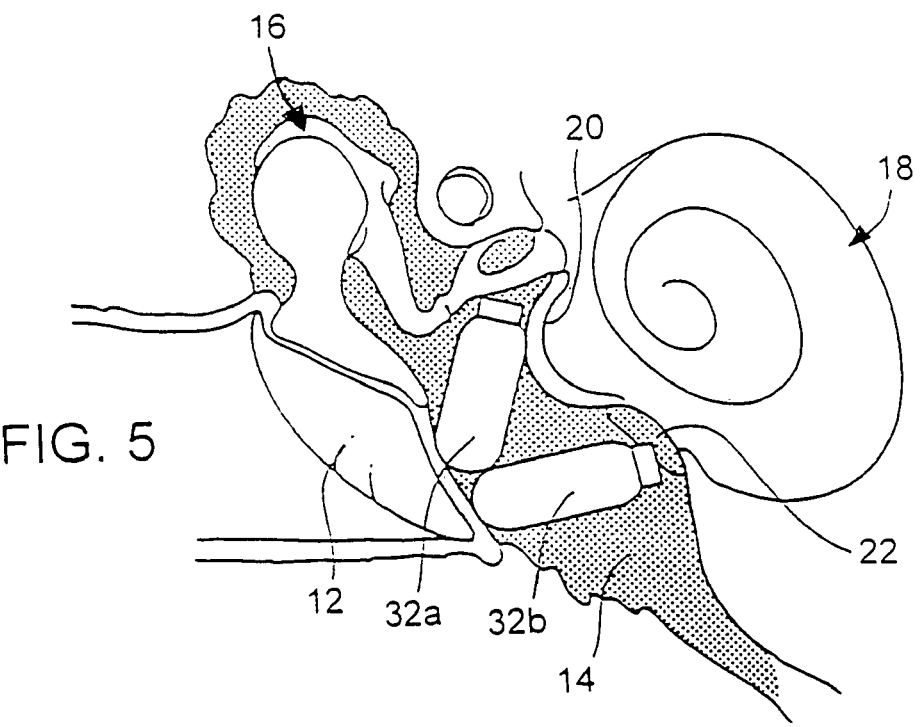
FIG. 5 illustrates two balloons, each similar to the balloons of FIG. 3, disposed in the middle ear such that both balloons contact the eardrum.

FIG. 5 illustrates an alternative practice of the present invention in which first and second balloons 32a, 32b are implanted into the middle-ear chamber 14. The first balloon 32a is disposed between a portion of the eardrum 12 and the promontory 20. The second balloon 32b is disposed between a portion of the eardrum 12 and the round window membrane 22. Hence, each of the first and second balloons 32a, 32b at least partially contacts the eardrum 12. The disposition of two balloons rather than a single balloon as shown in FIG. 5 provides presents two parallel impedances, rather than one, to the eardrum 12, thereby reducing the impedance load of to the eardrum 12. In effect, by using two balloons, the total volume of the implant is effectively increased. In other words, the total acoustic impedance of the two-balloon system of the illustrated balloons 32a and 32b is lower than the individual impedance of each balloon. An increase in the total volume advantageously improves the effectiveness of the implant for enhancing transmission of sound through the middle ear to the inner ear 10c, thereby ameliorating conductive hearing loss.

Figure 6:
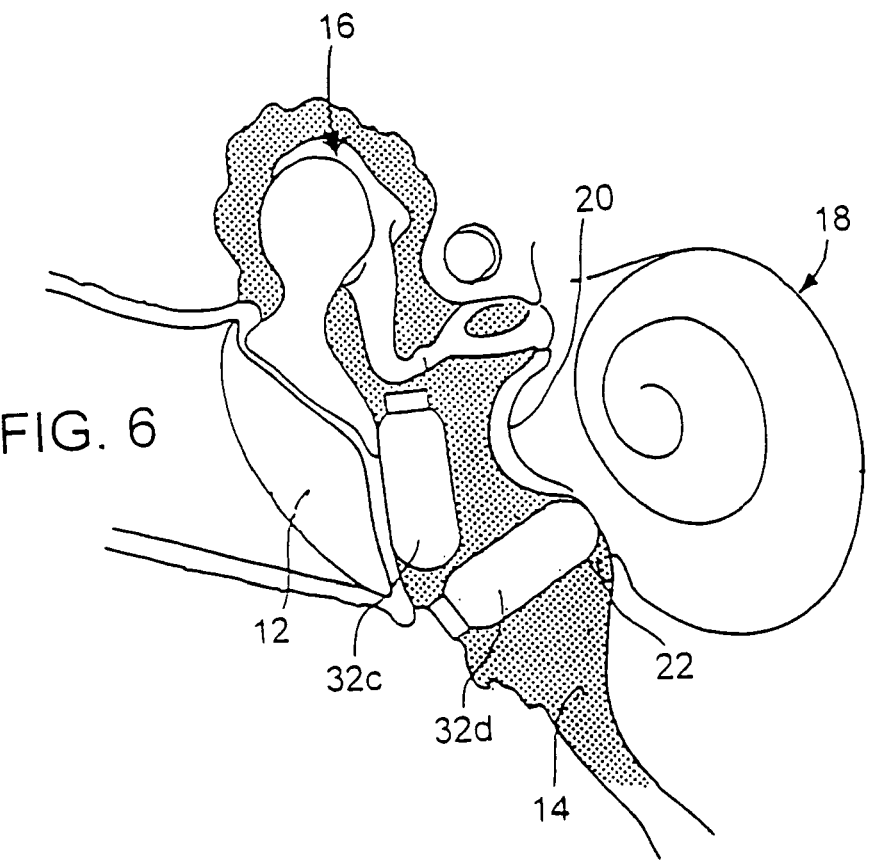
FIG. 6 illustrates the balloons of FIG. 5, disposed in the middle ear such that one balloon contacts the eardrum and the other balloon contacts the round window membrane without contacting the eardrum.

FIG. 6 illustrates yet another alternative practice of the invention in which first and second balloons 32c, 32d are disposed in the middle-ear chamber 14. In this embodiment, only the first balloon 32c contacts the eardrum 12. The second balloon 32d, which is not in contact with the eardrum 12, is disposed such that it contacts the round window membrane 22.

Those skilled in the art will recognize that the number of balloons that can be implanted in the middle ear is not necessarily limited to two. The size of the middle ear space of a particular patient and the size of the balloons employed typically dictate the maximum number of balloons that can be implanted in the middle-ear chamber.

A preferred method for implanting the one or more balloons is performed during tympanoplasty surgery. During the surgery, the middle ear is exposed by elevating a tympano-meatal flap, and one or more balloons 26 are inserted in the middle ear space between the eardrum 12 and the promontory 20 or round window membrane 22. At least one balloon 26 is placed in contact with the eardrum 12. The balloons can be positioned between the eardrum 12 and the bone covering the cochlea 18. The anatomical constraints of the middle ear keep the balloons in stable position. Absorbable tissue gel material, such as gel-foam or the like, can be packed around the implanted balloon to help stabilize the balloon in the middle ear space. The placement of the balloons in the middle ear can be combined with repair of the eardrum 12 and/or reconstruction of the ossicles 16.

While the present invention has been described with reference to above illustrative embodiments, those skilled in the art will appreciate that various changes in form and detail may be made without departing from the intended scope of the present invention as defined in the appended claims.

What we claim as new, and secured by Letters Patent is:

1. An implant for implantation in a middle-ear chamber, said implant comprising:
    a pliant membrane formed into a balloon having a physical volume, said balloon configured to fit within said middle-ear chamber and to contact an eardrum, wherein said balloon has an acoustic impedance corresponding to an equivalent volume of at least 70% of said physical volume.

2. The implant of claim 1, wherein said implant further comprises a tab extending from an end of said balloon.

3. The implant of claim 2 wherein said tab includes a radio-opaque marker.

4. The implant of claim 1, wherein said balloon is an ovaloid having a maximum dimension along a principal axis extending between a first end and a second end, and said implant further comprises a tab extending from at least one of said first and second ends.

5. The implant of claim 4, wherein said balloon is dimensioned to be positioned by surrounding structures within said middle-ear chamber and to displace fluid and soft tissue therefrom, thereby forming a compliant cushion presenting low acoustic impedance to motion of said eardrum.

6. The implant of claim 1, wherein said pliant membrane comprises polymer of vinyledene chloride (PVDC).

7. The implant of claim 1, wherein said pliant membrane comprises a biocompatible material.

8. The implant of claim 7, wherein said biocompatible material is a polymeric film free of toxic additives.

9. The implant of claim 7, wherein said pliant membrane is a multilayer membrane and said biocompatible material forms an outermost layer of said multilayer membrane, said outermost layer being exposed, upon implantation of said implant, to the interior of said middle-ear chamber.

10. The implant of claim 1, wherein said pliant membrane is substantially impermeable to water, gases and body fluids during protracted contact with body tissues.

11. The implant of claim 1 wherein said balloon contains at least one naturally occurring gas.

12. The implant of claim 1, wherein said balloon contains at least one non-naturally occurring gas.

13. The implant of claim 12, wherein said non-naturally occurring gas is a large molecular size gas which is non-toxic and to which said pliant membrane is substantially impermeable.

14. The implant of claim 12, wherein said non-naturally occurring gas is sulfur hexafluoride.

15. The implant of claim 1, wherein said balloon contains a gas mixture at atmospheric pressure.

16. The implant of claim 1, wherein said balloon contains a gas mixture having a pressure in the range of approximately 50 mm of water below atmospheric pressure to approximately 50 mm of water above atmospheric pressure.

17. The implant of claim 1, further comprising means for self-inflating said balloon, said self-inflating means including gas at sub-atmospheric pressure effective for self-inflation by diffusion following implantation of said implant into said middle-ear chamber.

18. The implant of claim 1, further comprising means for initiating self-inflation following implantation, said means for initiating self-inflation including gases at partial pressures effective to initiate self inflation.

19. The implant of claim 1, wherein said pliant membrane is between approximately 1 mil thick and approximately 4 mils thick.

20. An implant for implantation in a middle-ear chamber, said implant comprising:
a plurality of balloons, each of which is formed from a pliant membrane, each balloon having a physical volume and an acoustic impedance corresponding to an equivalent volume of at least 70% of said physical volume, said balloons configured to fit within said middle-ear chamber with at least one of said balloons at least partially in contact with the eardrum.

21. A surgical method for treating middle-ear hearing loss of a patient, said method comprising:
positioning a balloon in the patient's middle ear at least partially in contact with the eardrum, said balloon being formed of a thin pliant membrane of biocompatible material that defines a physical volume, said balloon having an acoustic impedance corresponding to an equivalent volume of at least 70% of said physical volume, said pliant membrane being substantially impermeable to water and to gases during extended contact with body tissues.

22. A surgical method according to claim 21, wherein positioning a balloon includes positioning the balloon between the eardrum and the bone covering the cochlea.

23. The surgical method of claim 21, further comprising positioning one or more additional balloons in the patient's middle-ear such that said additional balloons are mechanically coupled to said balloon.

24. A surgical method according to claim 21, further comprising exposing the patient's middle ear by elevating a tympano-meatal flap before disposing said balloon in the middle ear.

25. The surgical method of claim 24, further comprising securing said balloon into position with an anchor formed of resorbable packing.

* * * * *